: US 10,207,244 B2
(45) Date of Patent: Feb. 19, 2019

(12) United States Patent
Sarajlic

(54) METHOD OF MANUFACTURING A PLURALITY OF THROUGH-HOLES IN A LAYER OF FIRST MATERIAL

(71) Applicant: SMARTTIP BV, Enschede (NL)

(72) Inventor: Edin Sarajlic, Zutphen (NL)

(73) Assignee: SMARTTIP B.V., Enschede (NL)

( * ) Notice: Subject to any disclaimer, the term of this patent is extended or adjusted under 35 U.S.C. 154(b) by 0 days.

(21) Appl. No.: 15/444,010

(22) Filed: Feb. 27, 2017

(65) Prior Publication Data
US 2017/0246611 A1 Aug. 31, 2017

(30) Foreign Application Priority Data
Feb. 25, 2016 (NL) ..................................... 2016329

(51) Int. Cl.
*C23C 14/46* (2006.01)
*B01J 19/08* (2006.01)
(Continued)

(52) U.S. Cl.
CPC ....... *B01J 19/081* (2013.01); *A61B 5/150396* (2013.01); *B81C 1/0015* (2013.01); *B81C 1/00087* (2013.01); *B81C 1/00111* (2013.01); *B81C 1/00119* (2013.01); *C01B 21/0687* (2013.01); *C23C 14/0031* (2013.01); *C23C 14/46* (2013.01); *C23C 14/5833* (2013.01);
(Continued)

(58) Field of Classification Search
CPC .. C23C 14/0031; C23C 14/46; C23C 14/5833
See application file for complete search history.

(56) References Cited

U.S. PATENT DOCUMENTS 5,608,749 A * 3/1997 Kizuki ................. H01S 5/0201
372/36
6,156,215 A 12/2000 Shimada et al.
(Continued)

FOREIGN PATENT DOCUMENTS

WO 2012/098571 A1 7/2012

OTHER PUBLICATIONS

E. Sarajlic et al., Design, Fabrication and Characterization of an In-Plane AFM Probe With Ultra-Sharp Silicon Nitride Tip, Proceedings of the 21st Micromechanics and Micro Systems Eiurope Workshop (MME 2010), Sep. 26, 2010, pp. 24-27, Enschede, Netherlands.
(Continued)

*Primary Examiner* — Jason Berman
(74) *Attorney, Agent, or Firm* — Shewchuk IP Services, LLC; Jeffrey D. Shewchuk

(57) ABSTRACT

A method of manufacturing a plurality of through-holes in a layer of first material by subjecting part of the layer of said first material to ion beam milling.
For batch-wise production, the method comprises
after a step of providing the layer of first material and before the step of ion beam milling, providing a second layer of a second material on the layer of first material,
providing the second layer of the second material with a plurality of holes, the holes being provided at central locations of pits in the first layer, and
subjecting the second layer of the second material to said step of ion beam milling at an angle using said second layer of the second material as a shadow mask.

6 Claims, 9 Drawing Sheets

(51) Int. Cl.
  B81C 1/00    (2006.01)
  C01B 21/068  (2006.01)
  C23C 14/58   (2006.01)
  C23C 14/00   (2006.01)
  A61B 5/15    (2006.01)

(52) U.S. Cl.
  CPC . *B01J 2219/0879* (2013.01); *B81B 2201/057* (2013.01); *B81B 2201/12* (2013.01); *B81B 2203/0118* (2013.01); *B81B 2203/0353* (2013.01); *B81C 2201/0143* (2013.01)

(56) References Cited

U.S. PATENT DOCUMENTS

2005/0241374 A1* 11/2005 Schlaf .................... G01Q 70/12
                                                          73/105
2006/0165957 A1   7/2006  Oesterschulze et al.
2013/0305519 A1  11/2013  Sarajlic

OTHER PUBLICATIONS

Berenschot, Erwin J. W. et al., Fabrication of 2D-extruded fractal structures using repeated corner lithography and etching, 9th IEEE Int'l Conf Nano/Micro Engineered and Molecular Systems (NEMS), Apr. 13, 2014, pp. 374-377.

Deladi, S. et al., Fabrication of Micromachined Fountain Pen With In Situ Characterization Possibility of Nanoscale Surface Modification, Journal of Micromechanics & Microengineering, vol. 15, No. 3, Mar. 1, 2005, pp. 528-534, Institute of Physics Publishing, Bristol GB.

* cited by examiner

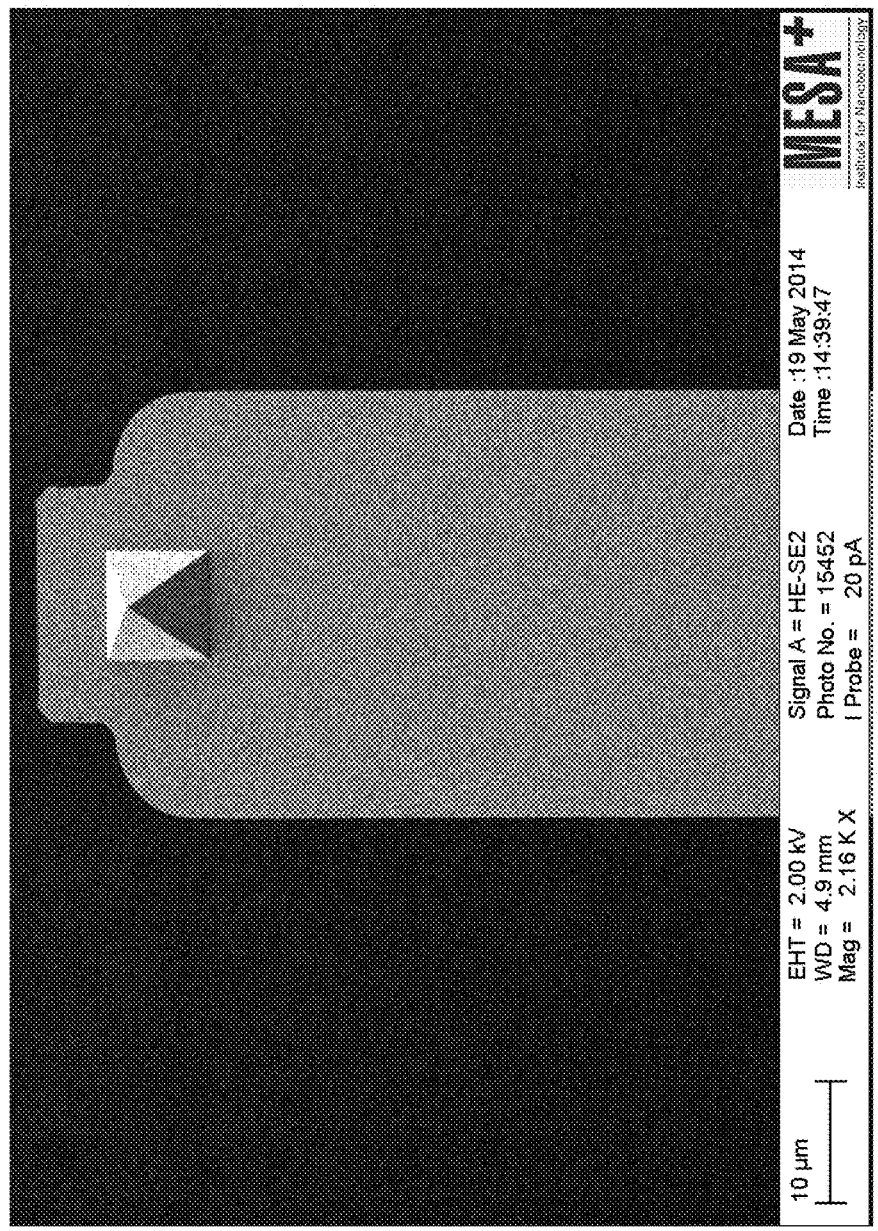

METHOD OF MANUFACTURING A PLURALITY OF THROUGH-HOLES IN A LAYER OF FIRST MATERIAL

The present invention relates to a method of manufacturing a plurality of through-holes in a layer of first material.

US2006/0165957 discloses a method of method of manufacturing a plurality of through-holes in a layer of material wherein an intermediate product is subjected to a plurality of method steps, the intermediate product
defining a first side and a second side, and
comprises a base substrate, said base substrate comprising a base material, wherein at the first side the surface of the base substrate defines a main plane;
wherein the plurality of method steps comprises the steps of
providing the base substrate of the intermediate product at the first side with a plurality of pits in said base material,
providing the base substrate with the layer of first material at the first side of the intermediate product, the first material being different from the base material so as to result in the intermediate product having pits comprising a layer of said first material,
providing a plurality of holes in the layer of first material at the central locations of the pits, and
subjecting the intermediate product to directional dry etching to provide holes in the base substrate.

Through-holes are provided by etching from the second side.

Various MEMS devices, such as i) probes comprising a hollow cantilever or ii) sieves, comprise at least one through-hole in a layer of first material such as silicon nitride. The through-hole is for example in a face of a pyramidal tip of the cantilever of a MEMS probe. MEMS probes comprising hollow cantilevers having a tip are used in life sciences for a variety of purposes, two of them being the delivery of a substance to or extraction of material from a cell. In that case, the tip of the MEMS probe will have to penetrate through the cell wall. Material of the cell wall should not clog the opening at the tip of the probe. For this reason, preference is given to probes having the opening (through-hole) in a side wall or pyramidal edge of the tip, instead of at the tip's distal end. In the art, probes with a cantilever comprising a conduit and having a tip are routinely produced. To create the opening of the conduit at the tip, use is made of focussed ion beam etching, wherein a beam of ions is focussed on a wall of a tip to locally etch said wall of first material and form the through-hole.

While MEMS techniques allow MEMS devices such as probes comprising cantilevers having a tip to be manufactured in large numbers simultaneously, this step of creating the opening (a through-hole) at the tip, has to be performed for each tip individually, and consecutively, which is time consuming and costly. Also, there is a risk of damage to the opposite wall of the tip once the focussed ion beam has penetrated the wall of the tip.

The objective of the present invention is to provide a method allowing for the creation of through-holes in a batch process, i.e. simultaneously creating a multitude of through-holes. It is a further object of the present invention to provide a method allowing for the batch-wise production of through-holes in pits comprising a layer of the first material, the through-holes being at a distance from the distal ends of said pits.

To this end, a method according to the preamble is characterized in that an intermediate product is subjected to a plurality of method steps, the intermediate product
defining a first side and a second side, and
comprises a base substrate, said base substrate comprising a base material, wherein at the first side the surface of the base substrate defines a main plane;
wherein the plurality of method steps comprises the steps of
providing the base substrate of the intermediate product at the first side with a plurality of pits in said base material, and
providing the base substrate with the layer of first material at the first side of the intermediate product, the first material being different from the base material so as to result in the intermediate product having pits comprising a layer of said first material,
providing a second layer of a second material that is different from the first material on the layer of first material, and
providing the second layer of the second material with a plurality of holes, the holes being provided at the central locations of the pits, and
with the second layer of the second material comprising the plurality of holes at central locations of the pits, subjecting part of the layer of said first material to ion beam milling to provide through-holes in the layer of first material by subjecting the first side of the base substrate provided with the second layer of the second material to said step of ion beam milling using said second layer of the second material as a shadow mask by having the ion beam at an angle α to the normal to the base main plane of at least 5°.

Thus, the layer of first material is subjected to ion beam milling, as a result of which at the central locations off-center holes are formed in said layer of first material. Subsequent removal of base material at the location of the pits will result in through-holes accessible from both the first side and the second side.

In the present application, the base substrate will in general be a wafer. The wafer is for example a silicon wafer, which may be used to manufacture probes comprising four-sided or three-sided pyramidal pits, as desired, depending on the crystal orientation of the starting wafer with respect to the base main plane. For four-sided and three-sided pyramidal tips these are 100 and 111 silicon respectively.

The method according to the invention is less sensitive to the processing conditions of the step of directional dry etching, because over etching merely results in damage to the base material of the substrate, which for many applications will be removed anyway.

After locally penetrating the layer of first material, the method will be continued using any conventional steps for manufacturing the MEMS device that is desired. By way of example, for a probe comprising a hollow conduit, a sacrificial conduit layer will be provided, followed by further wall material for the conduit covering said sacrificial conduit layer, and etching to remove the sacrificial conduit layer material, so as to result in a hollow conduit. Removing crystalline base material at the location of the pyramidal pit will result in a freely extending cantilever. Such methods are known in the art, for example from WO2012/096571.

According to a favourable embodiment, removing base material of the base substrate exposing the through-holes in the second layer of material.

It is preferred to remove the base material after creating the through-holes in the second layer, instead of before.

According to a favourable embodiment, the method comprises at least one further method step for manufacturing a plurality of MEMS devices, a MEMS device comprising a through-hole in the first layer.

A typical MEMS device according to the present invention is a probe, e.g. for taking a sample from a cell, or introducing material into a cell.

According to a favourable embodiment, the method comprises further steps for manufacturing a plurality of probes wherein
each probe of the plurality of probes comprises
a probe base section
having a probe base main plane, and
comprising a first opening of a conduit; and
a cantilever protruding from said probe base section parallel with the probe base main plane, said cantilever having
a proximal end connected to the probe base section, and
a distal cantilever end;
said cantilever comprising a tip having a distal tip end, said tip comprising a second opening of said conduit at a location away from the distal tip end;
wherein the second opening is formed by at least one step comprising the step of ion beam milling of the first layer of first material.

MEMS probes are an important application area and for the state of the art forming the second holes in a face of the tip is a major cost factor because so far they had to be milled individually with accurate aiming of a focussed ion beam. The present invention does not require focussed ion beam milling individual tips. The term "in a face" does not exclude that the hole is in two adjacent faces, i.e. crossing a pyramidal ridge.

According to a favourable embodiment, the probe comprises a hollow cantilever.

This is an important application area of the method according to the invention.

According to a favourable embodiment, the base material is a crystalline base material, and before the base substrate is provided with the first layer of first material, the method comprises the step of
etching the base substrate at the first side to form a plurality of pits in said crystalline base material, the pits comprising a face that is at an angle to the main plane.

Pits are typically formed using anisotropic etching of the base material, which allows for the formation of pyramidal pits. Thus MEMS techniques allow for the manufacture of probes having a sharp pyramidal tip. With a probe comprising a sharp tip, excessive damage to the cell is to be avoided. The probe may also serve a dual role, because the tip may be used for scanning using one of a variety of scanning techniques known in the art. A typical crystalline base material used in the art is silicon (1,0,0).

The face will extend along a crystal plane of the base material.

Phrased in two-part form, the invention related a method of manufacturing a plurality of through-holes in a layer of first material
wherein an intermediate product is subjected to a plurality of method steps, the intermediate product
defining a first side and a second side, and
comprises a base substrate, said base substrate comprising a base material, wherein at the first side the surface of the base substrate defines a main plane;
wherein the plurality of method steps comprises the steps of
providing the base substrate of the intermediate product at the first side with a plurality of pits in said base material, and
providing the base substrate with the layer of first material at the first side of the intermediate product, the first material being different from the base material so as to result in the intermediate product having pits comprising a layer of said first material, and
subjecting part of the layer of said first material to ion beam milling to provide through-holes in the layer of first material;
characterized in that
the method further comprises
after the step of providing the layer of first material and before the step of ion beam milling
providing a second layer of a second material that is different from the first material on the layer of first material, and
providing the second layer of the second material with a plurality of holes, the holes being provided at the central locations of the pits, and
with the second layer of the second material comprising the plurality of holes at central locations of the pits, subjecting the first side of the base substrate provided with the second layer of the second material to said step of ion beam milling using said second layer of the second material as a shadow mask by having the ion beam at an angle α to the normal to the base main plane of at least 5°. In conjunction with this, the invention relates to all the appended subclaims as well.

The present invention will now be illustrated with reference to the drawing where FIG. 1 shows a probe as can be manufactured using the method according to the invention, in top view (top) and cross-sectional view (bottom), both views being vertically aligned;

FIG. 2A to FIG. 2J illustrate a method of manufacturing the probe according to FIG. 1 in top view (top) and cross-sectional view (bottom), both views being vertically aligned;

FIG. 3a shows a Scanning Electron Microscope image of a probe manufactured according to the invention.

Figure 1:
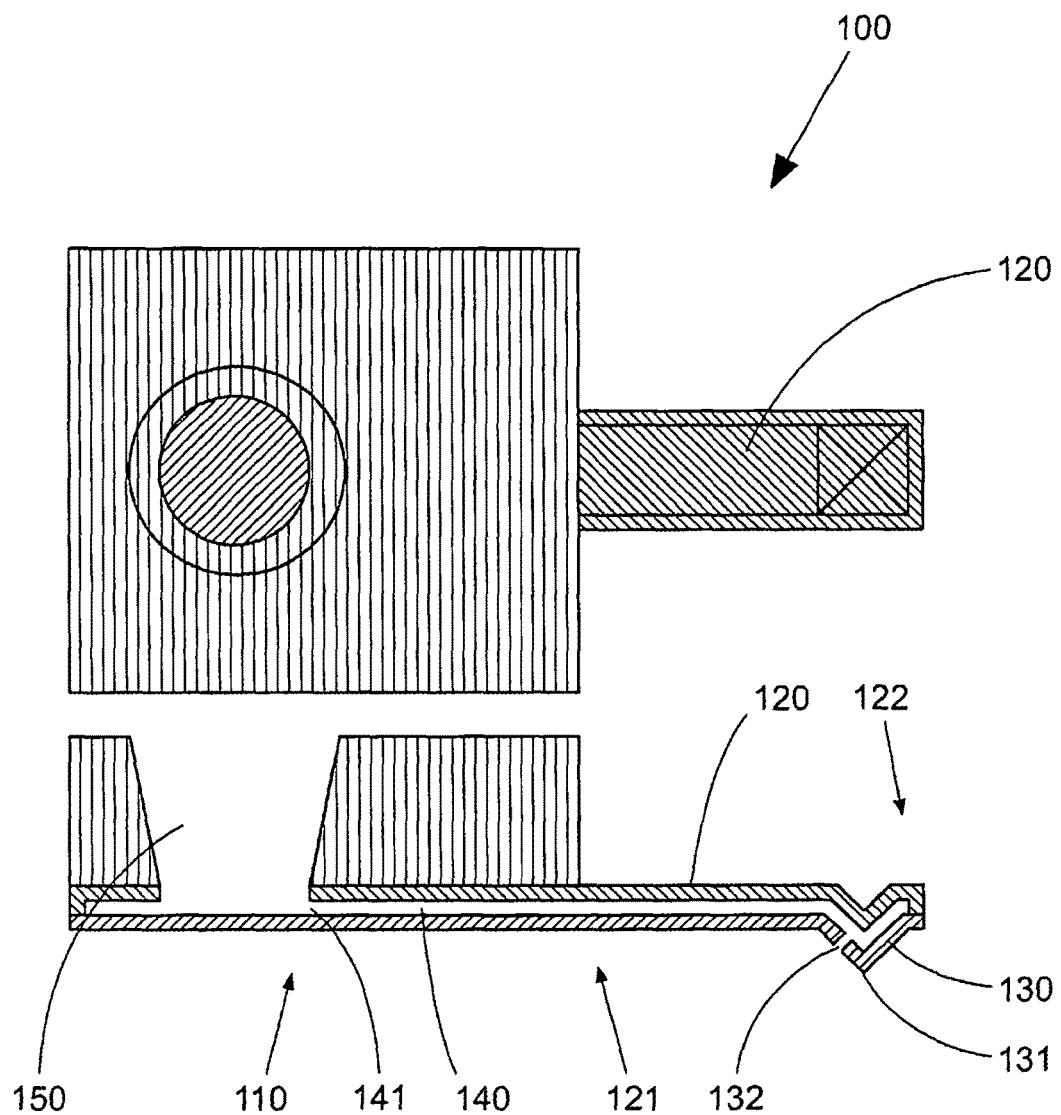
FIG. 1 shows a probe 100 as can be manufactured using the method according to the invention, in top view (top) and cross-sectional view (bottom), both views being vertically aligned.

The probe 100 comprises a probe base section 110 and a cantilever 120 extending from the probe base section 110. The cantilever 120 has a proximal end 121 connected to the probe base section 110 and a distal cantilever end 122.

The distal cantilever end 122 comprises a pyramidal tip 130 comprising a pyramidal tip end 131. In a face of the pyramidal tip 130, i.e. away from the pyramidal tip end 131, there is a through-hole 132 manufactured in accordance with the present invention.

The probe 100 comprises an elongated conduit 140 extending from a reservoir 150 at the probe base section 110 through the cantilever 120 to the through-hole 132.

The conduit 140 comprises a first opening 141 and the second opening is defined by the through-hole 132.

The method according to the invention will now be illustrated using FIG. 2A to FIG. 2J, which show in top view and cross-sectional view a method of manufacturing the probe 100 of FIG. 1. The method according to the present invention allows for a multitude of through-holes 132 and hence probes 100 to be manufactured at once, but the figures will show one probe 100 in the making only.

A silicon wafer 200 having a thickness of 380 um is shown (FIG. 2A) in top view. The silicon wafer 200 is of (1,0,0) silicon. If a pyramidal tip with three faces is desired, (1,1,1) silicon may be used instead.

Figure 2A:
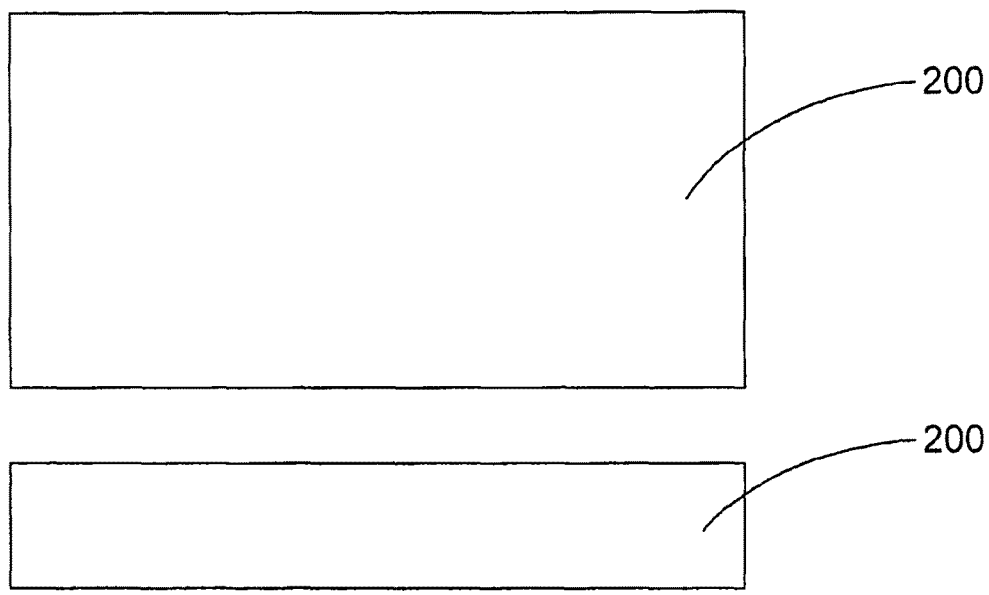
Figure 2B:
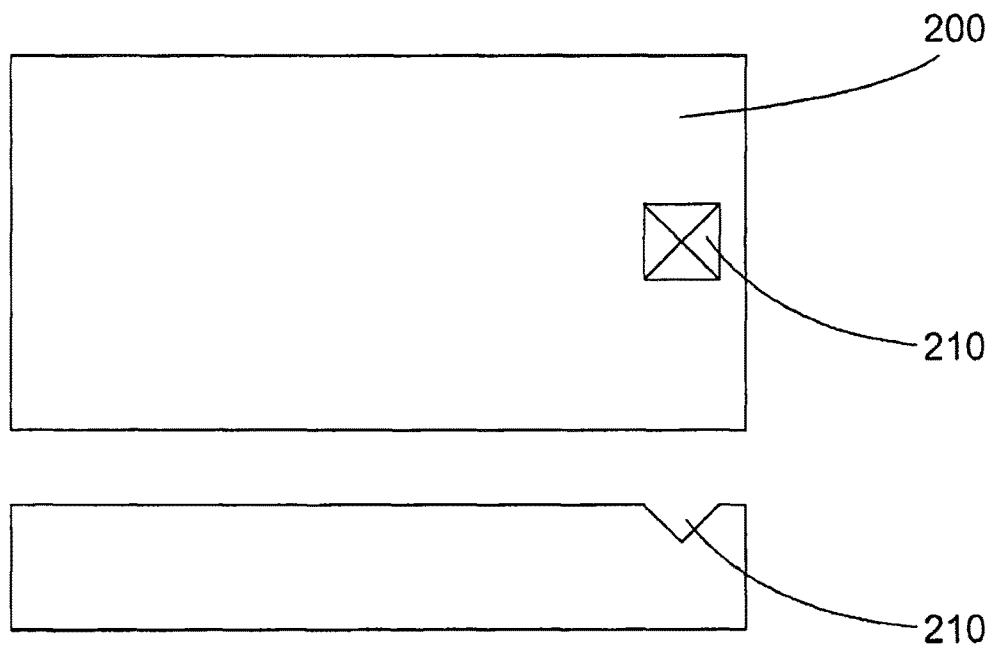

Using a mask, pyramidal pits 210 (only one shown, singulars are used in the remainder of the figure description) is etched by wet anisotropic etching of the silicon using 25% KOH (FIG. 2B). The pyramidal pit 210 is 10 um by 10 um.

Figure 2C:
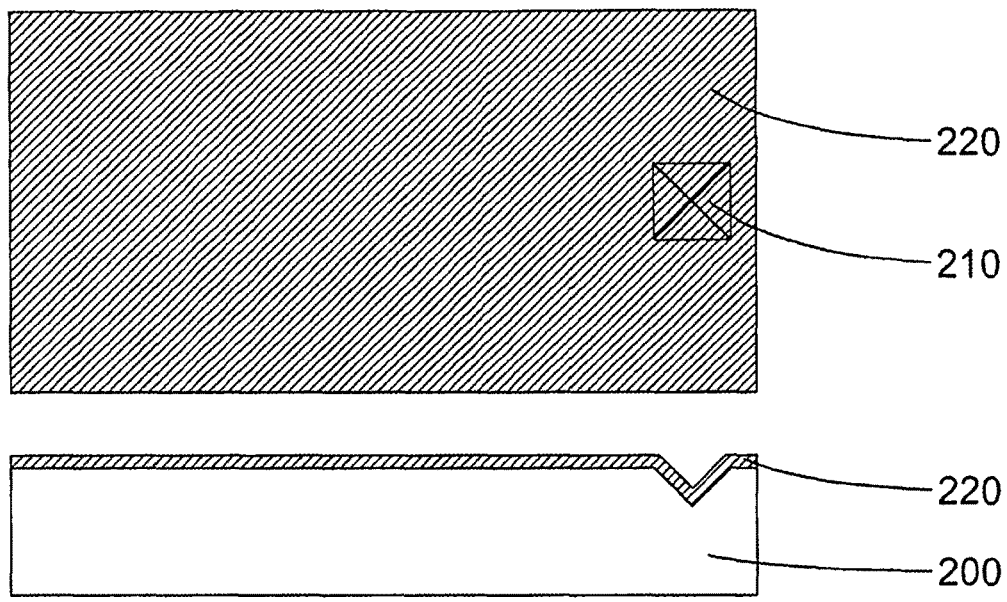

A thin layer of first material 220 (300 nm), here silicon nitride, is deposited (FIG. 2C) on the silicon wafer 200 comprising a pyramidal pit 210 (FIG. 2C). The silicon nitride will be part of a wall defining the conduit 140 and the pyramidal tip 130.

Figure 2D:
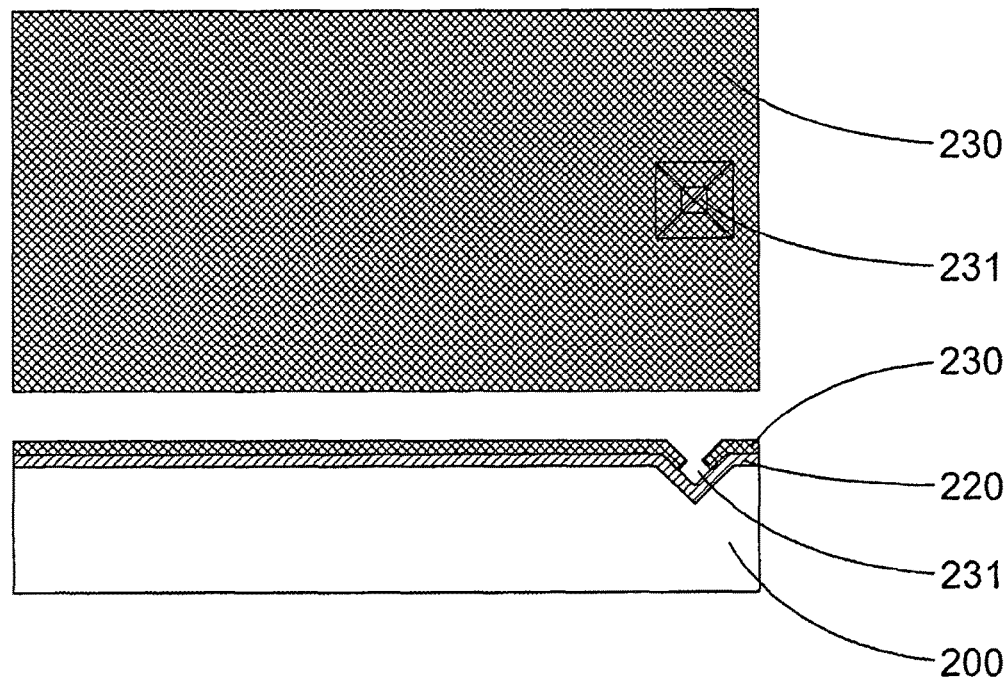
Figure 2E:
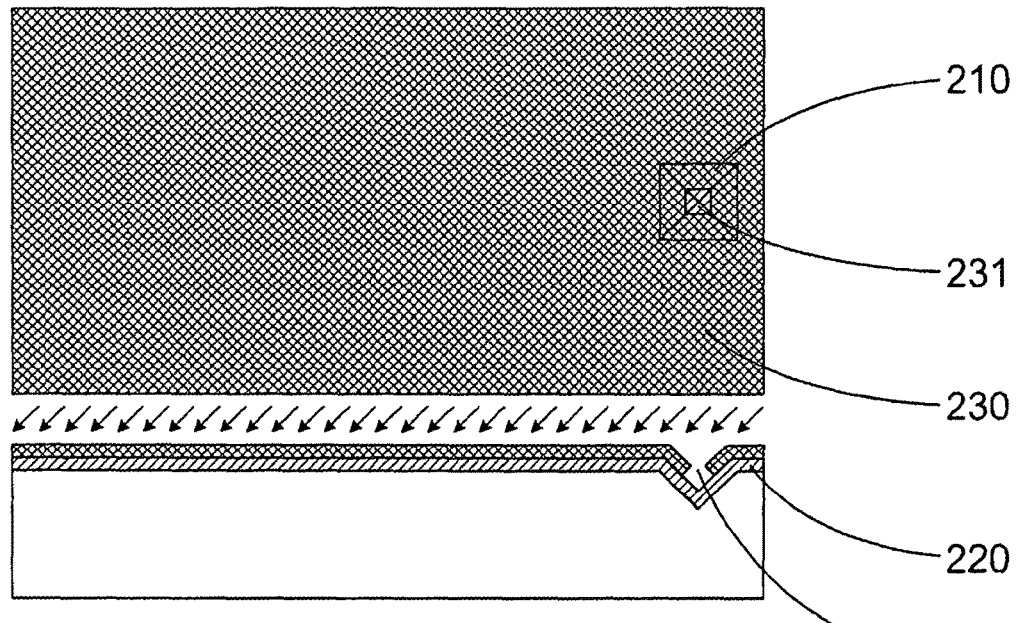

A thin layer of a second material 230 in this case 400 nm thick silicon oxide was formed as a masking material on top of the first layer of first material 220 and provided with a small opening 231 centrally located at the bottom of the pyramidal pit 210 using corner lithography (FIG. 2D).

Other techniques can be used instead, for example deposition of silicon oxide by Low Pressure or Plasma Enhanced Chemical Vapor Deposition (LPCVD or PECVD) followed by optical lithography and silicon oxide etching.

The central location of a pit is the location where the pit is the deepest. Typically the openings 231 are concentric holes.

The wafer 200 provided with the layer of silicon dioxide is etched using an ion beam at an angle by using an ion beam miller (FIG. 2E) using argon as inert gas. The angle α (with respect to the normal to the surface of the original wafer 200) was 25°.

Figure 2F:
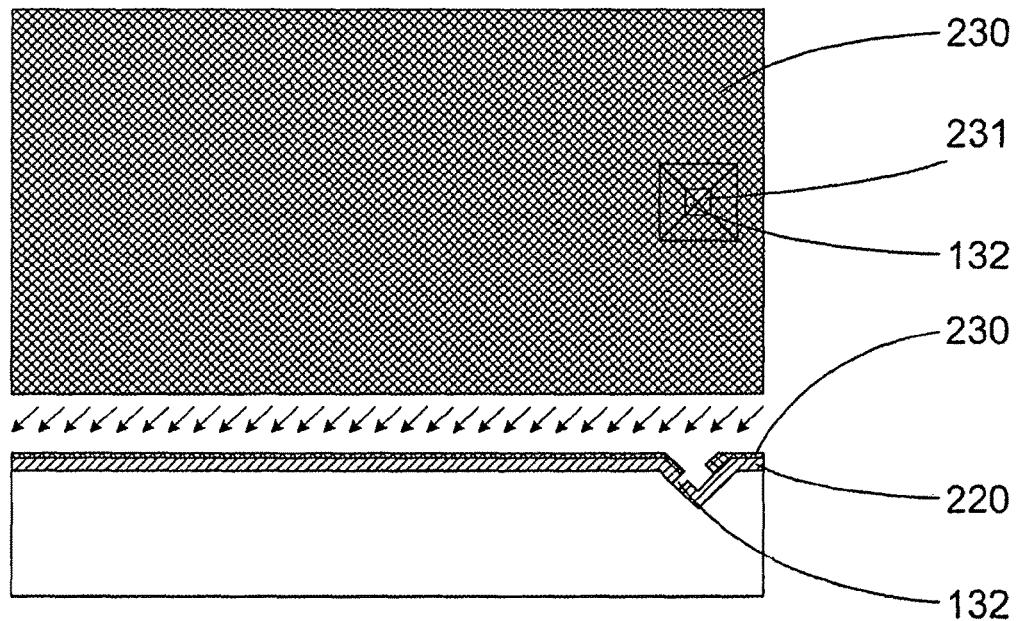

This results in an off-center through-hole 132 in the layer of first material 220 (FIG. 2F). Because a plurality of probes is manufactured using the present method, a plurality of through-holes 132 is formed at the same time, and not formed consecutively. The position of the through-hole 132 can to some extent be tuned by adjusting the etching angle α.

Figure 2G:
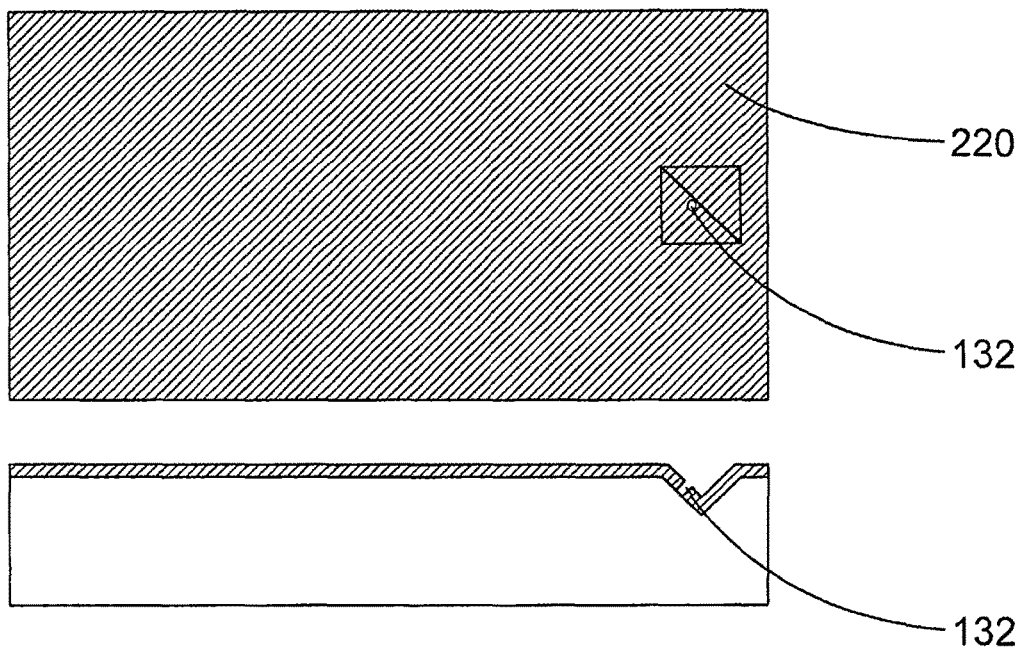

Now the silicon dioxide layer of second material 230, i.e. the layer that served as a masking material, is removed using hydrofluoric acid (HF) (FIG. 2G).

Figure 2H:
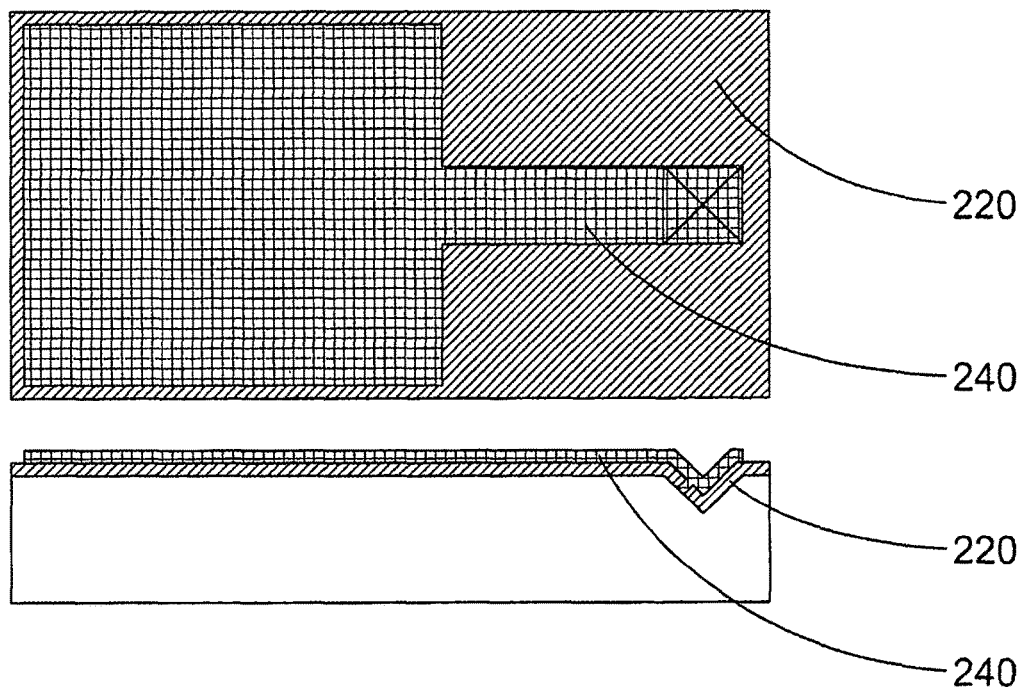
Figure 21:
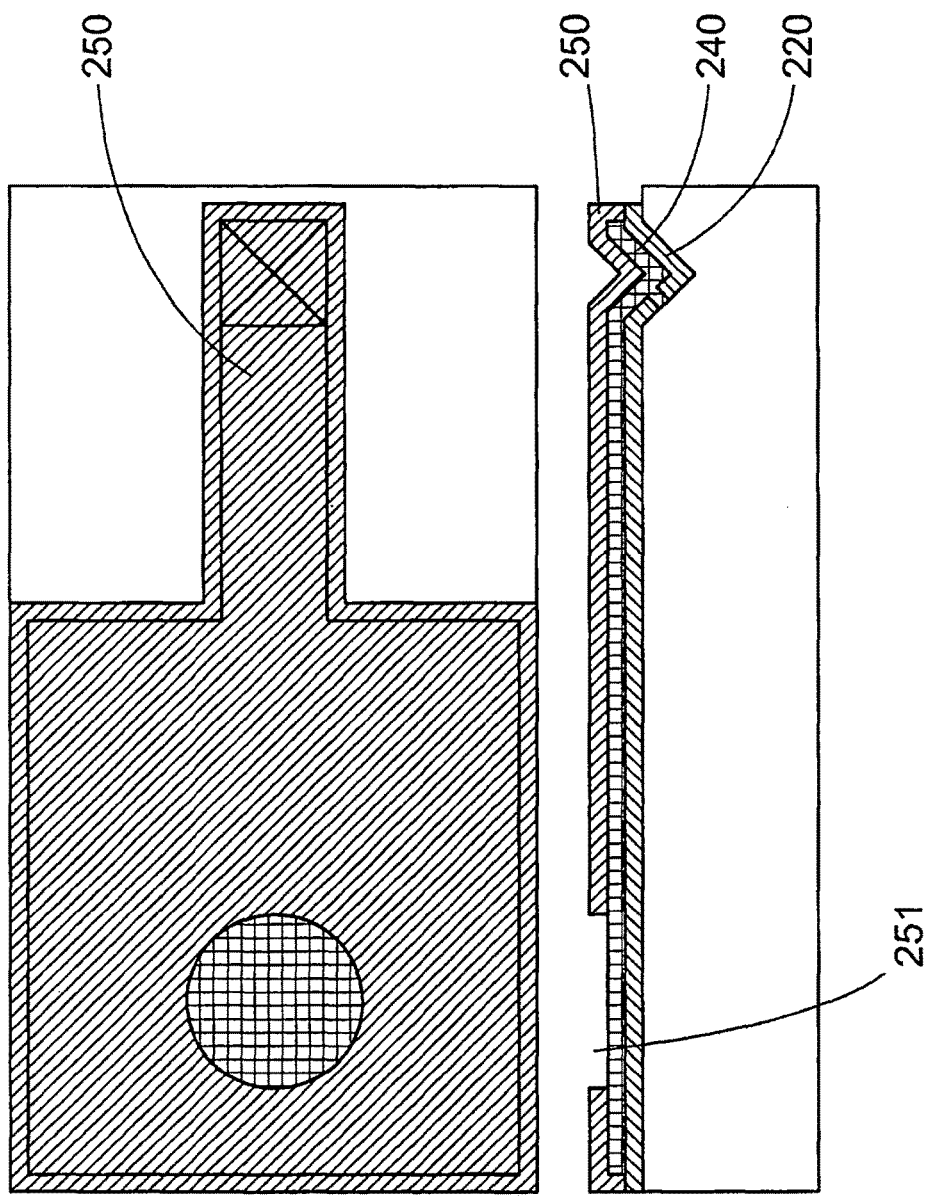

The remainder of the probe 100 is manufactured according to well-known practices, by providing the wafer obtained in the previous step with a patterned layer of sacrificial material 240, here polycrystalline silicon with a thickness of 1 um (FIG. 2H).

A further layer 250 of silicon nitride having a thickness of 300 nm is deposited, covering the silicon nitride layer of first material 220 and the layer of sacrificial material 240. It is subsequently etched by Reactive Ion Etching to create an etching window 251 so as to expose part of the sacrificial layer of material 240 at a location that will later on be at the probe base section 110.

Figure 2J:
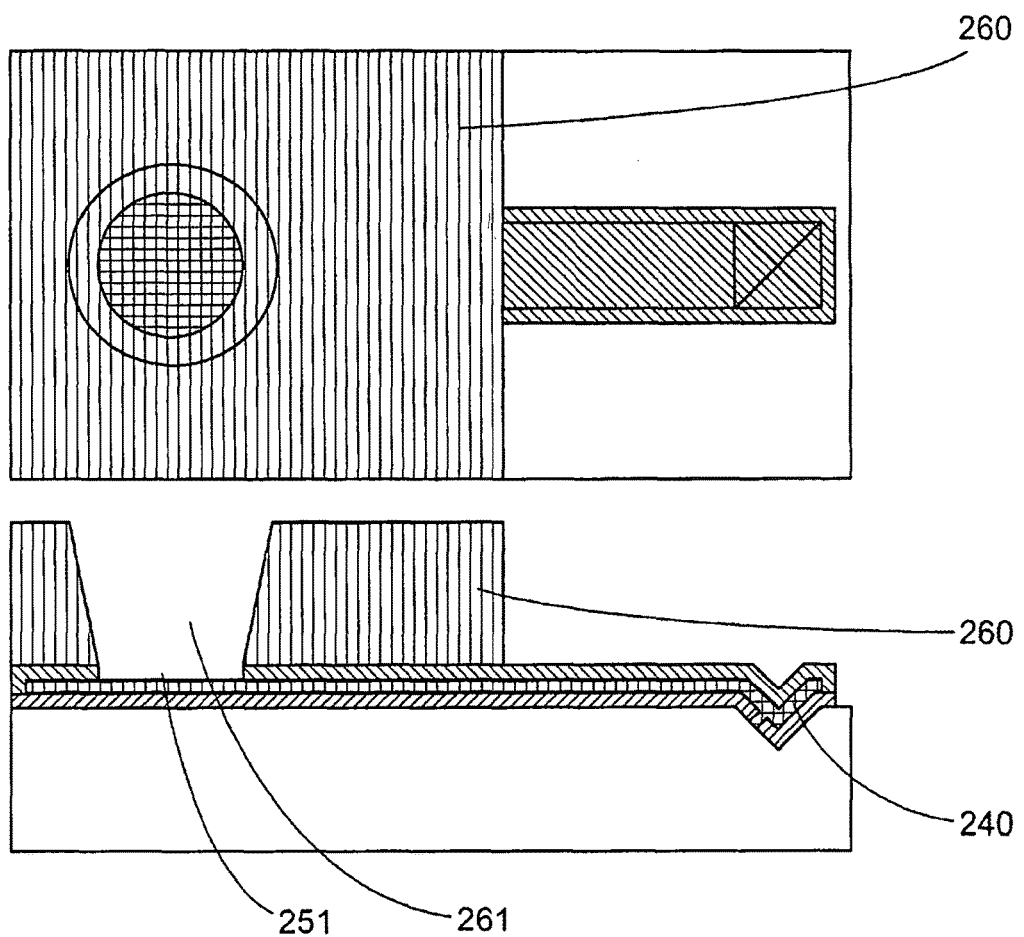

The further layer of material 250 is bonded to a glass cover 260 by anodic bonding (FIG. 2J). The glass cover 260 has a cover hole 261 (a through-hole) that will allow access of etchant to the polycrystalline sacrificial material at the location of the cover hole 261 and, once the silicon of the wafer has been etched away, at the through-hole 132.

Etching with hot Tetramethylammonium hydroxide (TMAH) solution results in the probe 100, shown in FIG. 1.

FIG. 3A shows a Scanning Electron Microscope image of a probe 100 manufactured according to the invention. The pyramidal tip 130 and cantilever 120 are visible. The through-hole 132 is too small to see.

Figure 3B:
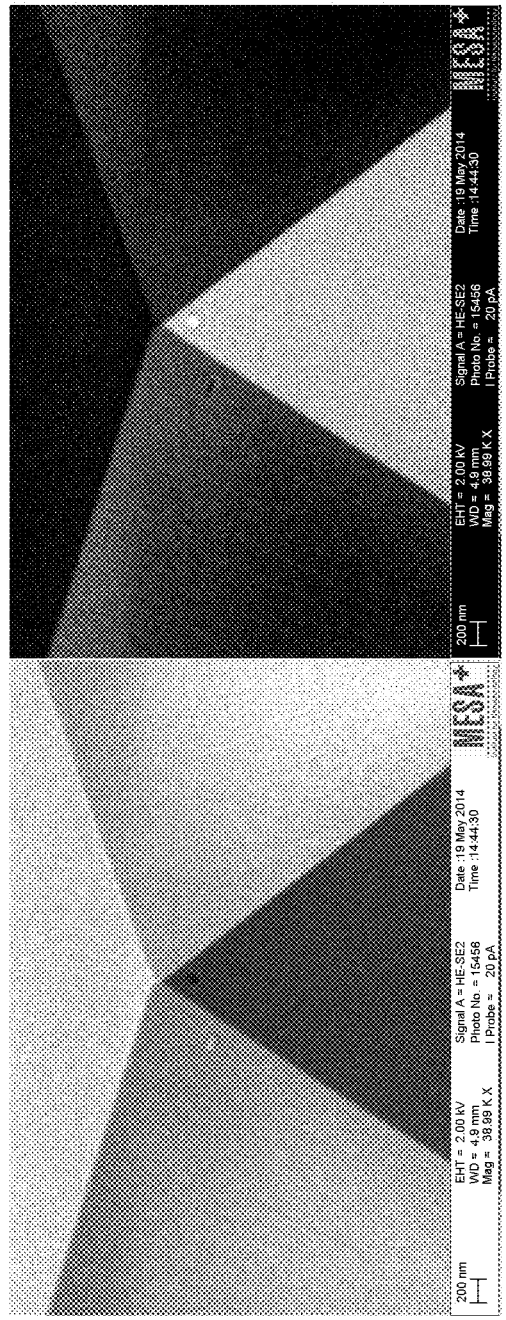
FIG. 3b shows a detail of the probe of FIG. 3A, with inverted gray scale at the right.

FIG. 3B shows a zoomed in SEM picture, showing a detail of the probe 100 of FIG. 3A. To avoid reproduction problems, the detail is shown with inverted gray scale tones at the right. The through-hole 132 is visible near the tip end 131 of the pyramidal tip 130.

The invention claimed is:

1. A method of manufacturing a plurality of through-holes in a layer of first material wherein an intermediate product is subjected to a plurality of method steps, the intermediate product
    defining a first side and a second side, and
    comprises a base substrate, said base substrate comprising a base material, wherein at the first side the surface of the base substrate defines a main plane;
wherein the plurality of method steps comprises the steps of
    providing the base substrate of the intermediate product at the first side with a plurality of pits in said base material, and
    providing the base substrate with the layer of first material at the first side of the intermediate product, the first material being different from the base material so as to result in the intermediate product having pits comprising a layer of said first material,
    providing a second layer of a second material that is different from the first material on the layer of first material, and
    providing the second layer of the second material with a plurality of holes, the holes being provided at the central locations of the pits, and
    with the second layer of the second material comprising the plurality of holes at central locations of the pits, subjecting part of the layer of said first material to ion beam milling to provide through-holes in the layer of first material by subjecting the first side of the base substrate provided with the second layer of the second material to said step of ion beam milling using said second layer of the second material as a shadow mask by having the ion beam at an angle α to the normal to the base main plane of at least 5°.

2. The method according to claim 1, wherein removing base material of the base substrate exposing the through-holes in the second layer of material.

3. The method according to claim 1, wherein the method comprises at least one further method step for manufacturing a plurality of MEMS devices, a MEMS device comprising a through-hole in the first layer.

4. The method according to claim 3, wherein the method comprises further steps for manufacturing a plurality of probes wherein
    each probe of the plurality of probes comprises
        a probe base section
            having a probe base main plane, and
            comprising a first opening of a conduit; and
        a cantilever protruding from said probe base section parallel with the probe base main plane, said cantilever having
            a proximal end connected to the probe base section, and
            a distal cantilever end;
            said cantilever comprising a tip having a distal tip end, said tip comprising a second opening of said conduit at a location away from the distal tip end;
    wherein the second opening is formed by at least one step comprising the step of ion beam milling of the first layer of first material.

5. The method according to any of the claims 3, wherein the probe comprises a hollow cantilever.

6. The method according to claim 1, wherein the base material is a crystalline base material, and before the base substrate is provided with the first layer of first material, the method comprises the step of
etching the base substrate at the first side to form a plurality of pits in said crystalline base material, the pits comprising a face that is at an angle to the main plane.

* * * * *